United States Patent
Endo et al.

(10) Patent No.: US 7,510,325 B2
(45) Date of Patent: Mar. 31, 2009

(54) PHANTOM AND PHANTOM ASSEMBLY

(75) Inventors: Masahiro Endo, Chiba (JP); Shinichiro Mori, Chiba (JP)

(73) Assignee: National Institute of Radiological Sciences, Anagawa, Inage-Ku Chiba-Shi Chiba (JP)

( * ) Notice: Subject to any disclaimer, the term of this patent is extended or adjusted under 35 U.S.C. 154(b) by 9 days.

(21) Appl. No.: 10/948,690

(22) Filed: Sep. 24, 2004

(65) Prior Publication Data

US 2005/0141672 A1 Jun. 30, 2005

(30) Foreign Application Priority Data

Dec. 24, 2003 (JP) ............................. 2003-427312

(51) Int. Cl.
*G01D 18/00* (2006.01)

(52) U.S. Cl. .................. 378/207; 378/18; 378/204; 250/252.1

(58) Field of Classification Search ............... 378/18, 378/163, 164, 207, 204; 250/252.1; 446/117, 446/118, 121, 122, 124, 125
See application file for complete search history.

(56) References Cited

U.S. PATENT DOCUMENTS

| | | | | |
|---|---|---|---|---|
| 3,867,638 A | * | 2/1975 | Golden | 378/145 |
| 4,040,630 A | * | 8/1977 | Brattain | 273/157 R |
| 4,163,152 A | * | 7/1979 | Suzuki | 250/374 |
| 4,390,101 A | * | 6/1983 | Humphreys et al. | 211/41.17 |
| 4,527,057 A | * | 7/1985 | Guyton et al. | 250/252.1 |
| 4,613,754 A | * | 9/1986 | Vinegar et al. | 250/252.1 |
| 4,692,704 A | * | 9/1987 | Gray | 324/318 |
| 4,818,943 A | * | 4/1989 | Chandra | 324/318 |
| 4,873,707 A | * | 10/1989 | Robertson | 378/18 |
| 5,095,499 A | * | 3/1992 | Wentz | 378/37 |
| 5,235,628 A | * | 8/1993 | Kalender | 378/207 |
| 5,442,674 A | * | 8/1995 | Picard et al. | 378/20 |
| 5,511,107 A | * | 4/1996 | Sliski | 378/207 |
| 5,793,835 A | * | 8/1998 | Blanck | 378/4 |
| 5,799,059 A | * | 8/1998 | Stembridge et al. | 378/207 |
| 6,296,541 B1 | * | 10/2001 | Bezalel et al. | 446/105 |
| 6,302,582 B1 | * | 10/2001 | Nord et al. | 378/207 |
| 6,364,529 B1 | * | 4/2002 | Dawson | 378/207 |
| 6,459,772 B1 | * | 10/2002 | Wiedenhoefer et al. | 378/163 |
| 6,585,412 B2 | * | 7/2003 | Mitschke | 378/207 |
| 6,648,715 B2 | * | 11/2003 | Wiens et al. | 446/121 |
| 6,679,780 B1 | * | 1/2004 | Shih | 273/157 R |
| 6,715,918 B2 | * | 4/2004 | Mitschke et al. | 378/207 |
| 6,739,752 B2 | * | 5/2004 | Sabczynski et al. | 378/207 |
| 6,843,761 B1 | * | 1/2005 | Uchida et al. | 492/40 |
| 6,974,254 B2 | * | 12/2005 | Paliwal et al. | 378/207 |
| 7,056,019 B1 | * | 6/2006 | Hanson et al. | 378/207 |
| 2005/0008126 A1 | * | 1/2005 | Juh et al. | 378/207 |

OTHER PUBLICATIONS

W. Leitz et al., "Computed Tomography Dose Assessment—A Practical Approach" Radiation Protection Dosimetry, vol. 57, Nos. 1-4, pp. 377-380 (1995).

Thomas B. Shope et al. "A Method For Describing the Doses Delivered by Transmission X-Ray Computed Tomography", Med. Phys. 8(4), Jul./Aug. 1981; pp. 488-495.

International Standard, IEC 60601-2-44, 2001, Amendment 1, Sep. 2002 "Particular Requirements for the Safety of X-ray Equipment for Computed Tomograghy"; pp. 1-6.

* cited by examiner

*Primary Examiner*—Allen C. Ho
(74) *Attorney, Agent, or Firm*—Squire, Sanders & Dempsey, LLP

(57) ABSTRACT

A phantom assembly includes a plurality of cylindrical shaped phantoms connectable to each other and/or a plurality of column-shaped phantoms connectable to each other with fitting portions. An x-ray radiation measuring device for measuring an x-ray radiation from an x-ray CT device is inserted in a through-hole of the phantom.

15 Claims, 9 Drawing Sheets

PHANTOM AND PHANTOM ASSEMBLY

BACKGROUND OF THE INVENTION

1. Field of the Invention

The present invention relates to a phantom and a phantom assembly (phantom unit) used as a dummy for a human body in assessing CT dosage of x-ray radiation, and is based on Japanese Patent Application No. 2003-427312, filed on Dec. 12, 2003, the disclosure of which is incorporated herein by reference.

2. Description of Related Arts

In a conventional assessment of CT dose, phantoms according to IEC (International Electrotechnical Commission) have been used (For example, see International Electrotechnical Commission, "Evaluation and routine testing in medical imaging departments constancy tests-x-ray equipment for computed tomography," pub. IEC, 1223-2-6 (1994); T. B. Shope, R. M. Gane, and G. C. Johnson, "A method for describing the doses delivered by transmission x-ray computed tomography," Med. Phys. 8, 448-495 (1981); and W. Leitz, B. Axelsson, and G. Szendro, "Computed tomography does assessment-A practical Approach." Radiat. Prot. Dosim., 57, 377-380 (1995)). In this case, for example, two phantoms, one for body portion, and another for head, are ready and each made of an acrylic resin and formed into a cylinder having a diameter of 320 mm and 160 mm, respectively, and a length of 150 mm. Cavities of 10 mm diameter were located parallel to the central axis of the cylinders, and the centers of the holes were located at the cylinder center and also 10 mm below the cylinder surface at 90 degree intervals (detailed in IEC document), and evaluation of x-ray irradiated onto a human body has been made by inserting a device for measuring dose.

In the conventional assessment of CT dose as described above, if conical beam having a large beam width of x-ray, what is called, cone beam is assessed by utilizing the phantoms, the phantoms should be form in a shape where the length of the shaft direction is large to meet the shape of the cone beam. In this case, weight and the size of the phantom are increased, inconvenient for carrying the phantom and for storing it. As a result, only an x-ray having a narrow beam width can be assessed by the conventional phantom.

When an x-ray is irradiated on such a phantom, the x-ray induces scattered radiation within the phantom, which is scattered distributed at random. Accordingly, when the assessment of the x-ray radiation (patient dose) including the scattered radiation will be made, the weight and the size of the phantom will be much more increased, leading to inconvenience in terms of portability and storage of the phantom. (For dose assessment for the cone-beam, although the weight of the phantom will be increased, the phantom length should be longer than the conventional one, because the scattered radiation is distributed wider than that in the narrow beam width.)

In order to overcome the inadequacy just mentioned, it can be considered that edges portion of phantoms are lined up in a face-to-face manner whereby the length of the phantoms in the shaft direction is set to be large as a whole. However, lining up of the phantoms has problems that fixation of the phantoms is incomplete and that x-ray radiation is passed through from gaps between the edge portions of the phantoms and, thus, no accurate assessment can be made. In order to make a long phantom from a practical point of view, we joined unit phantoms together to provide phantoms of the necessary length.

An object of the present invention is to provide a phantom and a phantom assembly which can easily be carried, in which the length of the phantom can be freely set to meet the shape of an x-ray beam, in which phantoms can be tightly connected, and which can assess CT dose of x-ray radiation in an accurate manner without passing the radial from phantoms. By inserting acrylic sticks through these holes, the cylinders were more tightly fixed to each other. Moreover, the connection portion of the phantoms was step-shaped so as not to allow direct passage of x-rays through any gaps.

SUMMARY OF THE INVENTION

According to a first aspect of the present invention, there is provided a phantom with which an x-ray radiation from an x-ray CT device is irradiated, comprising:

a fitting portion formed on at least one edge portion of the edge portions of both sides in the shaft direction, and a plurality of through-holes which are pierced through the shaft direction of the phantom.

In a preferred embodiment, the phantom according to the present invention possesses a totally column-shaped through-hole and the central portion thereof is pierced through the shaft direction of the phantom.

In a preferred embodiment, the phantom according to the present invention possesses a totally cylindrical-shaped through-hole having a hollow portion in which the hollow portion is pierced through the shaft direction of the phantom.

According to a second aspect of the present invention, there is provided a phantom assembly comprising:

a plurality of the phantoms according to the present invention connected with each other at the fitting portions thereof; and an x-ray radiation measuring device for measuring an x-ray radiation from an x-ray CT device, which has been projected in the through-holes.

In a preferred embodiment, a stick or sticks is/are inserted into a part or whole of gaps generated by the through-holes for embedding the gaps.

More preferably, a stick is arranged over two ore more phantoms.

According to a third aspect of the present invention, there is a provided a phantom assembly, comprising a plurality of the phantoms according to the present invention, possessing through-holes having a cylindrical shape each having a hollow portion as a whole in which the hollow portion is pierced through the shaft direction of the phantom, connected with each other at the fitting portions thereof;

a plurality of the phantoms according to the present invention, possessing through-holes having a column shape as a whole and the central portion thereof is pierced through the shaft direction of the phantom inserted into said hollow portions; and an x-ray radiation measuring device for measuring an x-ray radiation from an x-ray CT device projected in the through-holes.

In a preferred embodiment, a stick or sticks is/are inserted into a part or whole of gaps generated by the through-holes except for the portion having the x-ray radiation from an x-ray CT device inserted therein, for embedding the gaps.

More preferably, a stick is arranged over two ore more phantoms.

BRIEF DESCRIPTION OF THE DRAWINGS

FIG. 5 is a drawing showing one first column-shaped phantom in FIG. 3, wherein

FIG. 6 is a drawing showing one second column-shaped phantom in FIG. 3, wherein

FIG. 7 is a drawing showing one third column-shaped phantom in FIG. 3, wherein

FIG. 8 is a drawing showing one first cylindrical phantom in FIG. 4, wherein

FIG. 9 is a drawing showing one second cylindrical phantom in FIG. 4, wherein

FIG. 10 is a drawing showing one third cylindrical phantom in FIG. 4, wherein

FIG. 11 is a drawing showing one stick in FIG. 4, wherein

BEST MODES FOR CARRYING OUT THE INVENTION

The phantoms and the phantom assemblies according to embodiments of the present invention will now be described by referring to FIG. 1 to FIG. 11.

In the following description, the term "column-shaped phantom" used herein intended to encompass circular solid-, oval solid-, and in some cases, polygonal solid-phantoms. Also, the term "cylindrical shaped" used herein is intended to encompass circular hollow-, oval hollow-, and in some cases, polygonal hollow-phantoms.

Figure 1:
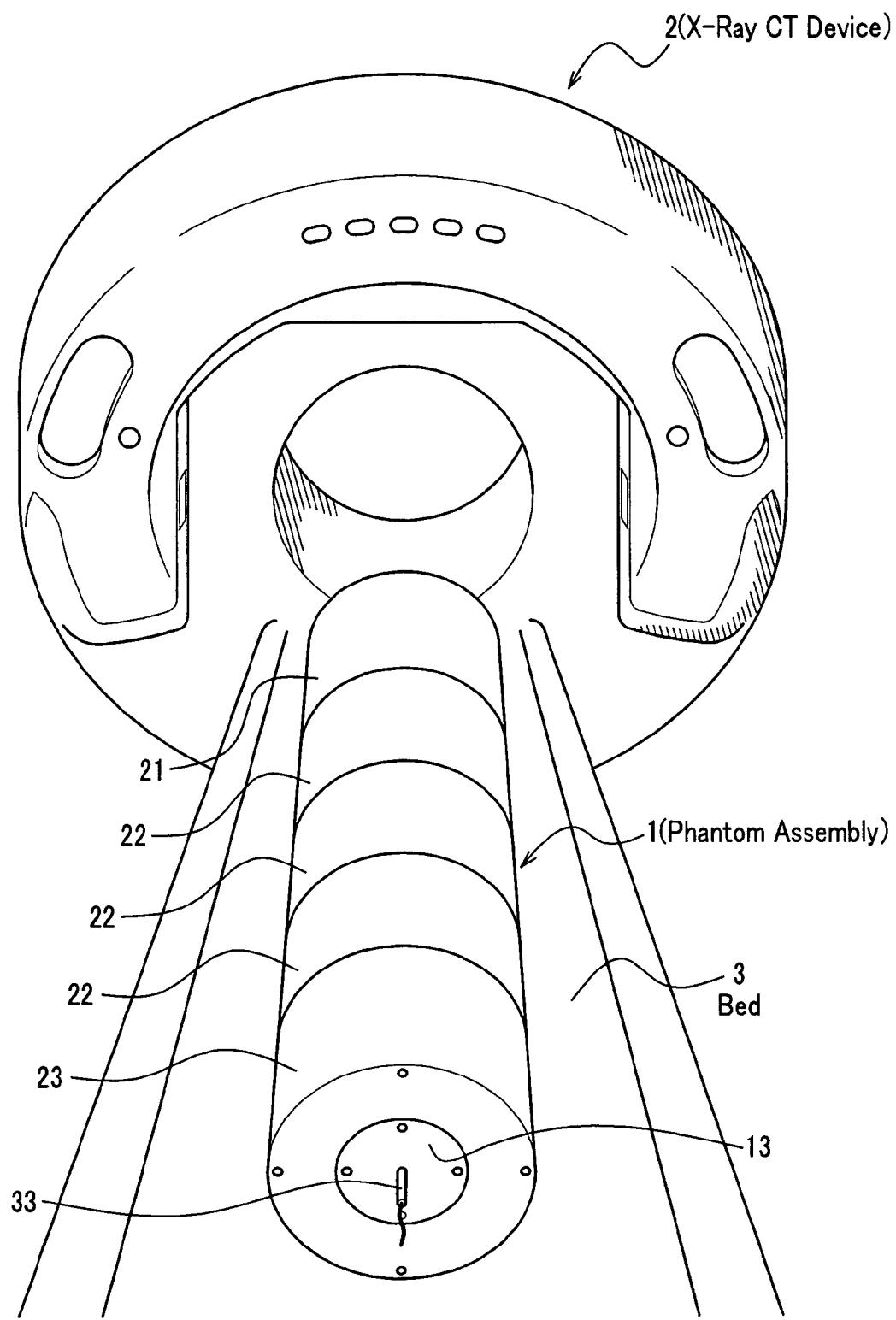
FIG. 1 is a perspective view showing an x-ray CT device and a phantom assembly according to one embodiment of the present invention.
Figure 2:
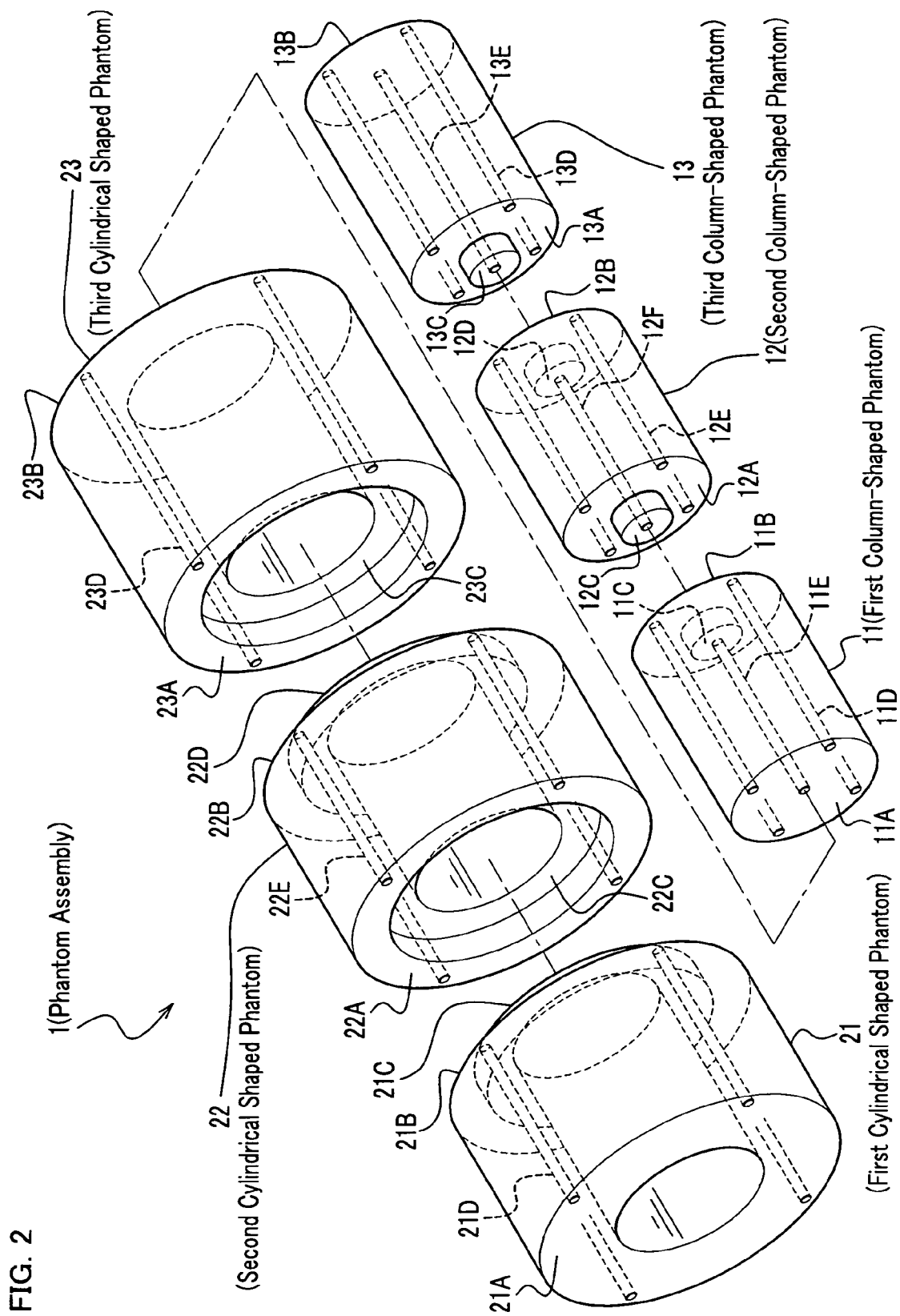
FIG. 2 is an expansion perspective view of the phantom assembly in FIG. 1.

FIG. 1 is a perspective view showing an x-ray CT device and a phantom assembly according to one embodiment of the present invention, and FIG. 2 is an expansion perspective view of the phantom assembly in FIG. 1.

As shown in FIG. 1, a phantom assembly 1 made of an acrylic resin assuming as a human body is placed on a bed 3 on which a patient is lying, and at this state, an x-ray radiation from an x-ray CT device 1 is irradiated on the phantom 1 to measure an x-ray radiation irradiated onto a human body.

Figure 3:
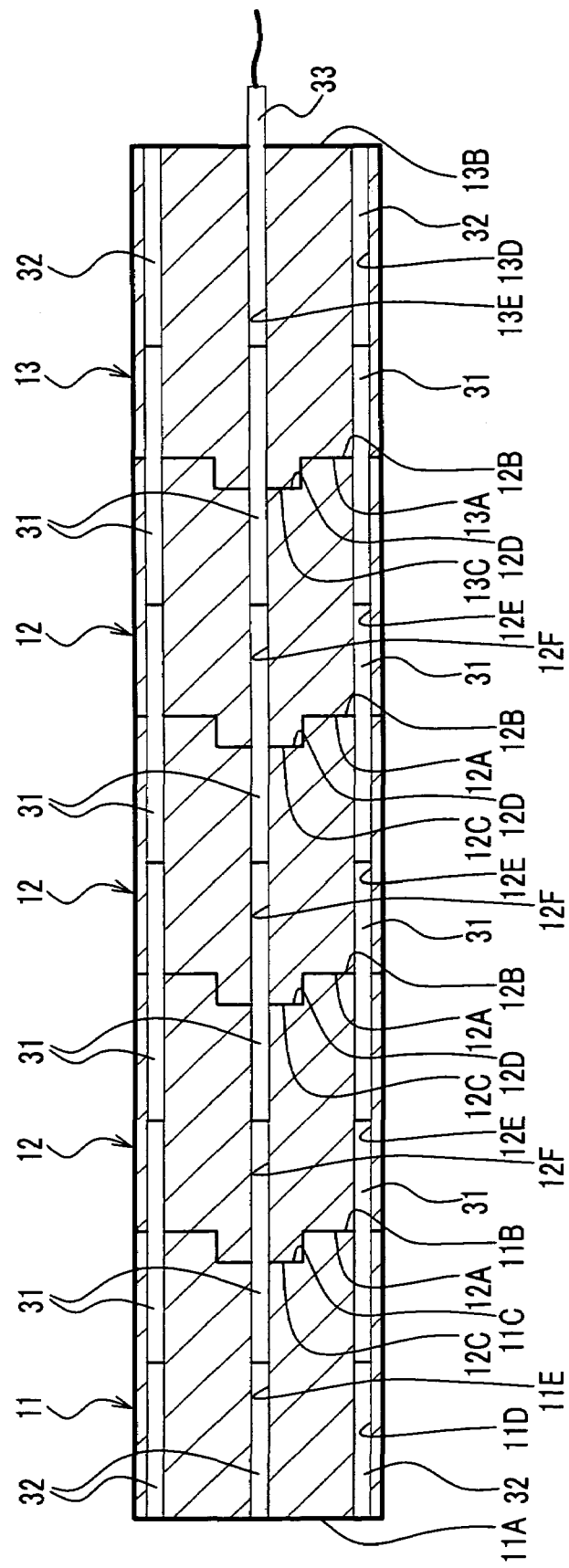
FIG. 3 is a longitudinal cross-sectional view showing a column-shaped phantom phantoms according to the present invention in the state where they are assembled.
Figure 4:
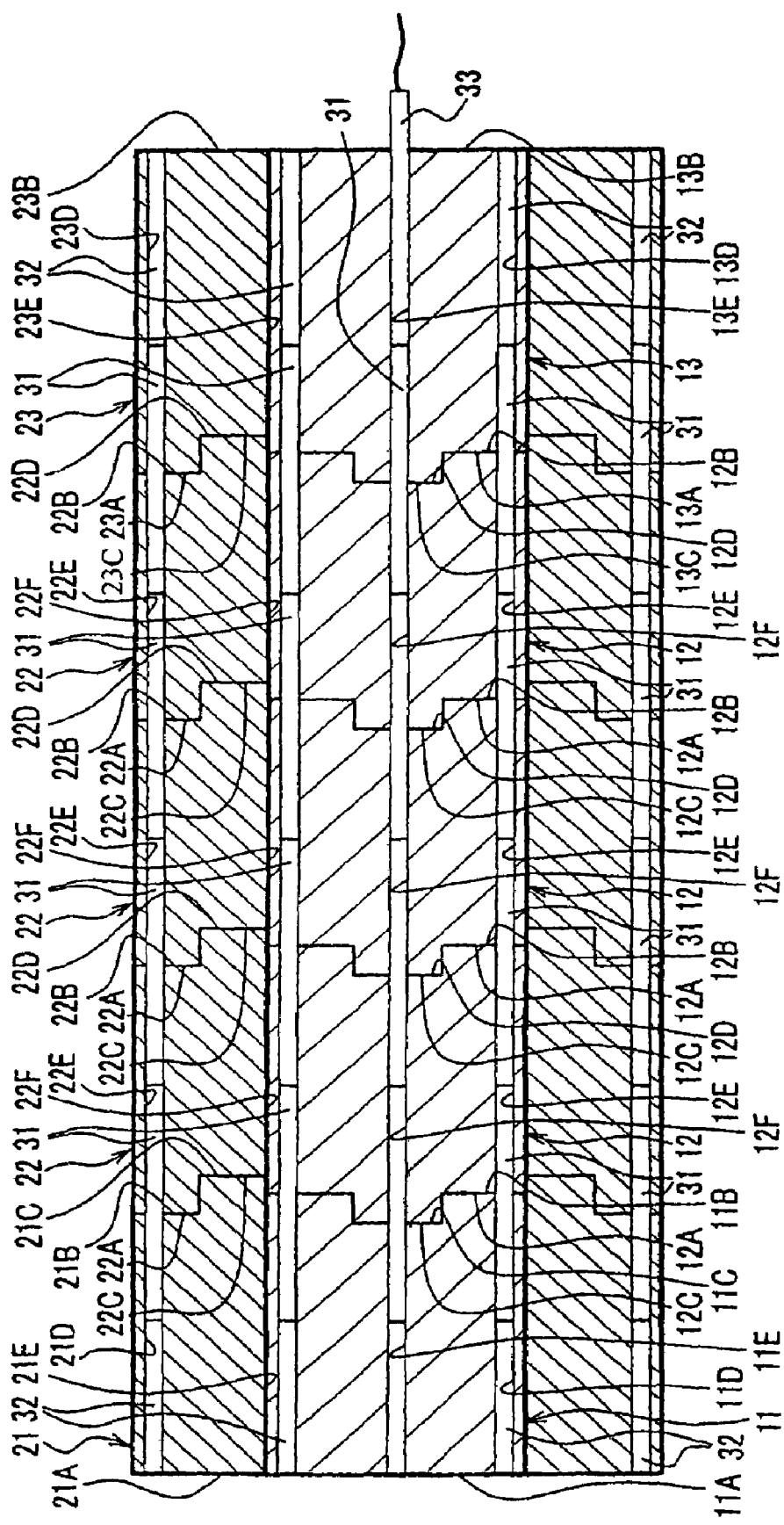
FIG. 4 a longitudinal cross-sectional view showing a cylindrical phantom phantoms according to the present invention in the state where they are assembled.
Figure 11A:
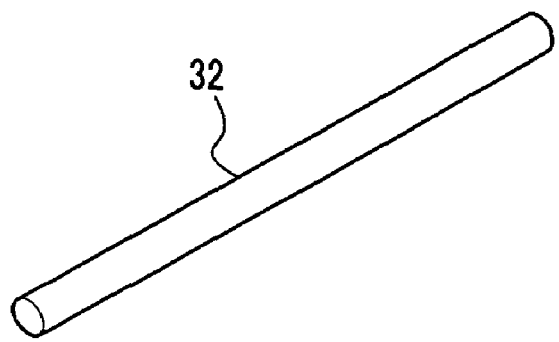
FIG. 11A is a perspective view showing one stick.
Figure 11B:
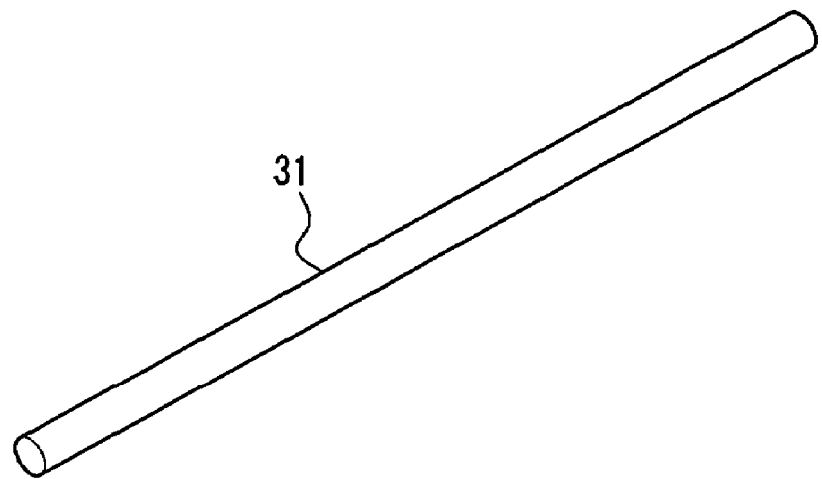
FIG. 11B is a perspective view showing another stick.

The phantom assembly 1 according to this embodiment will now be described. As shown in FIG. 2 and FIG. 3, the phantom assembly 1 possesses a first column-shaped phantom 11, a second column-shaped phantoms 12, 12, 12 (only one phantom shown in FIG. 2), and a third column-shaped phantom 13. Also, as shown in FIG. 2 and FIG. 4, the phantom assembly 1 possesses a first cylindrical phantom 21, a second cylindrical phantoms 22, 22, 22 (only one phantom shown in FIG. 2), and a third cylindrical phantom 23. As shown in FIG. 3, FIG. 4, and FIG. 11, the phantom assembly 1 also possesses a plurality of sticks 31 and 32 (only one stick shown in FIG. 1), which are column-shaped rod member, and a device 33 for measuring dose.

The cylindrical phantoms 21, 22, and 23 are used as a dummy for measuring dose on a human body. For example, the cylindrical phantom 23 shown in FIG. 2 produced may have an outer diameter of 160 mm to be used for measuring dosage on a head portion; while the cylindrical phantom 22 shown in FIG. 2 produced may have an outer diameter of 320 mm and the cylindrical phantom 23 may be inserted into the hollow portion thereof to be used for measuring dosage on a body portion. This reduces total production cost. Through-holes 11E, 12F, and 13E are provided for the purpose of the device 33 for measuring dose into the phantom assembly 1. The device 33 for measuring dose measures a strength of the x-ray radiation which is irradiated from the x-ray CT device 2 and arrived at the device 33 while the strength is attenuated during the passage through phantoms 11, 12, 13, 21, 22, and 23 depending upon the passing distance. Each of sticks 31 and 32 is embedded into spaces of the through-holes 11D, 11E, 12E, 12F, 13D, 13E, 21D, 22D, and 23D, to make dose assessment much more accurate.

Figure 5A:
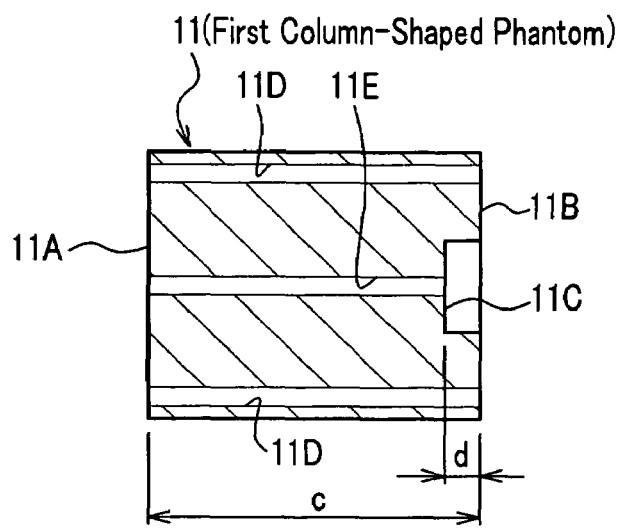
FIG. 5A is a longitudinal cross-sectional view of the first column-shaped phantom.
Figure 5B:
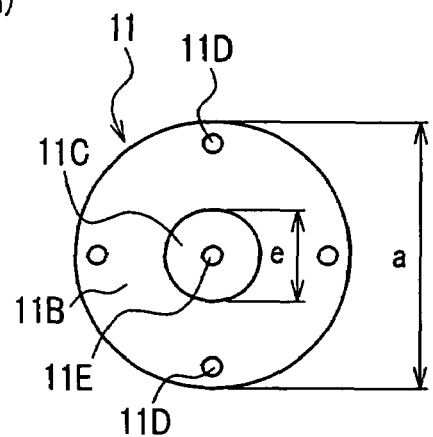
FIG. 5B is a right side view of the first column-shaped phantom.

As shown in FIG. 2 and FIG. 5, the first column-shaped phantom 11 has edge portions 11A and 11B perpendicular to the shaft direction at both sides of the shaft direction. One edge portion 11A of the first column-shaped phantom 11 perpendicular to the shaft direction is formed as a circular flat surface. In contrast, another edge portion 11B of the first column-shaped phantom 11 perpendicular to the shaft direction has a concave portion 11C for fitting, which is a fitting portion and which has a concave cross-section (formed as a circular hole having a bottom) provided thereon. Four through-holes 11D extending along the shaft direction and opening towards both edge portions 11A and 11B are formed on the column-shaped phantom 11 at equal intervals in the circumference direction. Another through-holes 11E are also formed on the column-shaped phantom 11 at a central portion along the shaft direction. Both ends of the through-hole 11E are opening towards the edge portion 11A and the concave portion 11C for fitting. As shown in FIG. 5, the column-shaped phantom 11 is formed so as to have an outer diameter [size a] and to have a length in the shaft direction [size c]. The depth of the concave portion 11C for fitting is size d and the hole size of the concave portion 11C for fitting is size e.

Figure 6A:
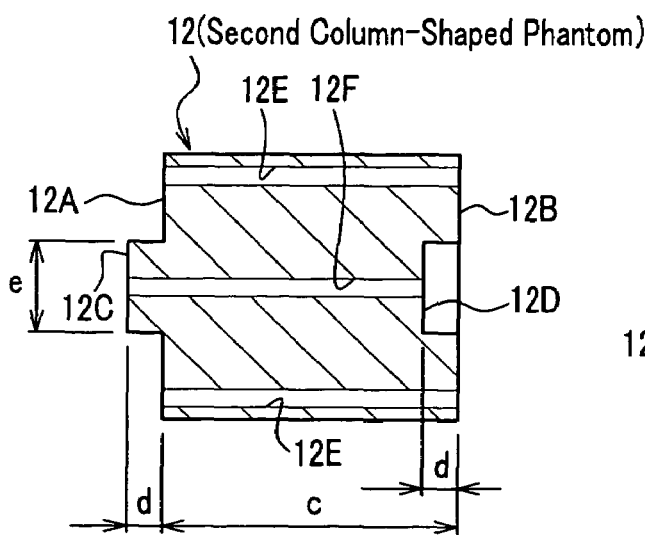
FIG. 6A is a longitudinal cross-sectional view of the second column-shaped phantom.
Figure 6B:
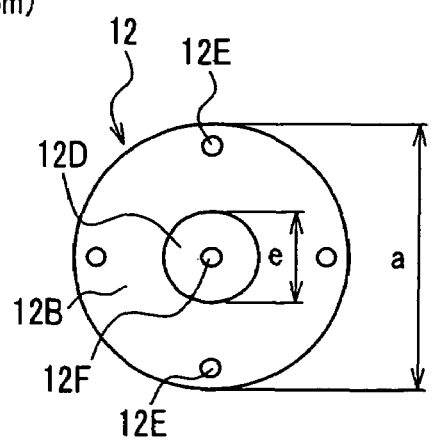
FIG. 6B is a right side view of the second column-shaped phantom.

As shown in FIG. 2 and FIG. 6, the second column-shape phantom 12 has edge portions 12A and 12B perpendicular to the shaft direction at both sides of the shaft direction. One edge portion 12A of the second column-shaped phantom 12 perpendicular to the shaft direction has a convex portion 12C for fitting, which is a fitting portion and which has a convex cross-section (formed as a circular column-shaped projection portion) provided thereon. In contrast, another edge portion 12B of the second column-shaped phantom 12 perpendicular to the shaft direction has a concave portion 12D for fitting, which is a fitting portion and which has a concave cross-section (formed as a circular hole having a bottom) provided thereon. Similar to the first column-shaped phantom 11, four through-holes 12E are formed on the column-shaped phantom 12 at equal intervals in the circumference direction, and another through-holes 12F are also formed on the column-shaped phantom 12 at a central portion. As shown in FIG. 6, the column-shaped phantom 12 is formed so as to have an outer diameter [size a] and to have a length in the shaft direction [size c]. The height of the projection possessed by the convex portion 12C for fitting is size d and the depth of the concave portion 12D for fitting is also size d. Further, the outer diameter of the convex portion 12C for fitting and the hole size of the concave portion 12D for fitting are size e.

Figure 7A:
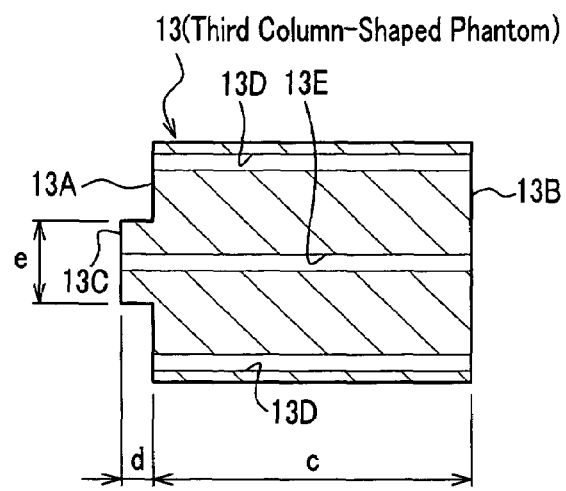
FIG. 7A is a longitudinal cross-sectional view of the third column-shaped phantom.
Figure 7B:
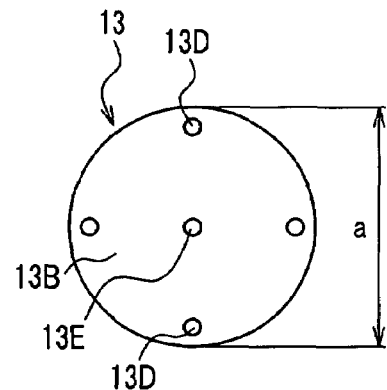
FIG. 7B is a right side view of the third column-shaped phantom.

As shown in FIG. 2 and FIG. 7, the third column-shaped phantom 13 has edge portions 13A and 13B perpendicular to the shaft direction at both sides of the shaft direction. One edge portion 13A of the third column-shaped phantom 13 perpendicular to the shaft direction has a convex portion 13C for fitting, which is a fitting portion and which has a convex-cross-section, (formed as a circular column-shaped projection portion) provided thereon. Similar to the first column-shaped phantom 11, four through-holes 13D are formed on the column-shaped phantom 13 at equal intervals, and another through-holes 13E are also formed on the column-shaped phantom 13 at a central portion. As shown in FIG. 7, the column-shaped phantom 13 is formed so as to have an outer diameter [size a] and to have a length in the shaft direction [size c]. The height of the convex portion possessed by the convex portion 13C for fitting is size d and the outer diameter of the convex portion 13C for fitting is size e.

Figure 8A:
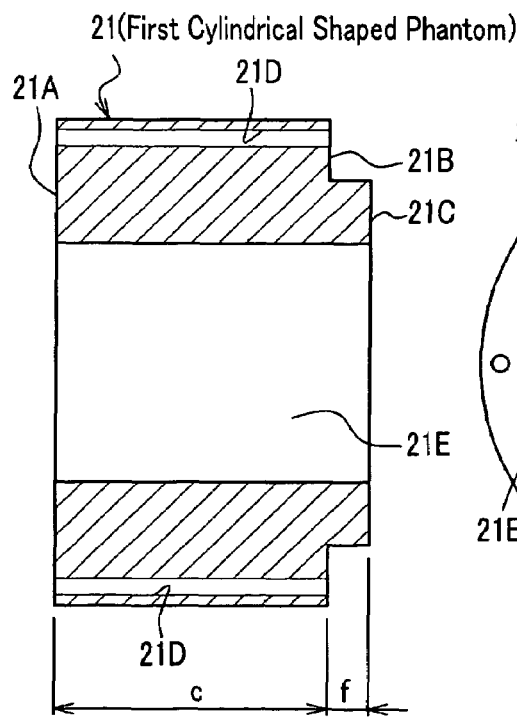
FIG. 8A is a longitudinal cross-sectional view of the first cylindrical phantom.
Figure 8B:
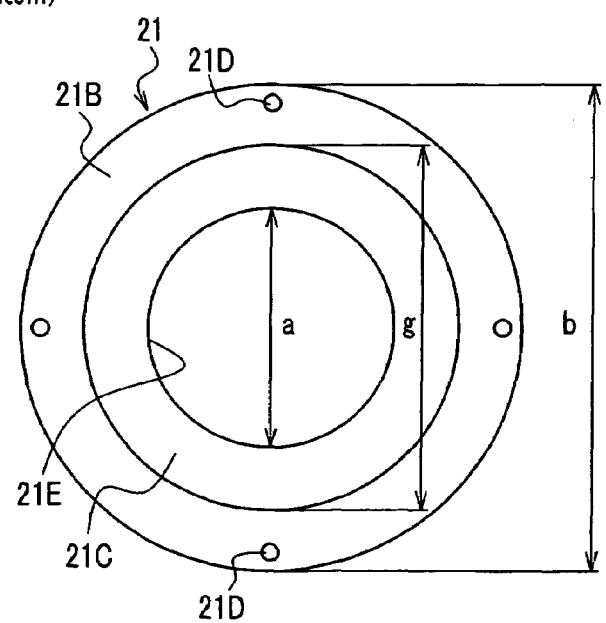
FIG. 8B is a right side view of the first cylindrical phantom.

As shown in FIG. 2 and FIG. 8, the first cylindrical phantom 21 has edge portions 21A and 21B perpendicular to the shaft direction at both sides of the shaft direction. One edge portion 21A of the first cylindrical phantom 21 perpendicular to the shaft direction is formed as a ring-shaped flat surface. In contrast, another edge portion 21B of the first cylindrical phantom 21 perpendicular to the shaft direction has a cylindrical projection 21C, which is a fitting portion, formed thereon. Four through-holes 21D are formed on the cylindrical phantom 21 at equal intervals in the circumference direction. As shown in FIG. 8, the inner diameter of the hollow portion 21E is set to be size a. Consequently, into the hollow portion 21E of the cylindrical phantom 21 can be inserted the column-shaped phantom 11, which has an outer diameter of size a with no space. The cylindrical phantom 21 is formed so as to have an outer diameter [size b] and to have a length in the shaft direction [size c]. The height of the projection of the convex portion 21C for fitting is size f and the outer diameter size of the convex portion 21C for fitting is set to be size g.

Figure 9A:
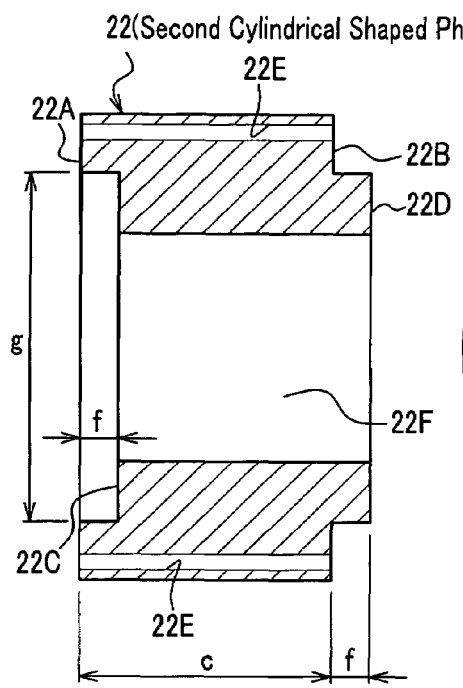
FIG. 9A is a longitudinal cross-sectional view of the second cylindrical phantom.
Figure 9B:
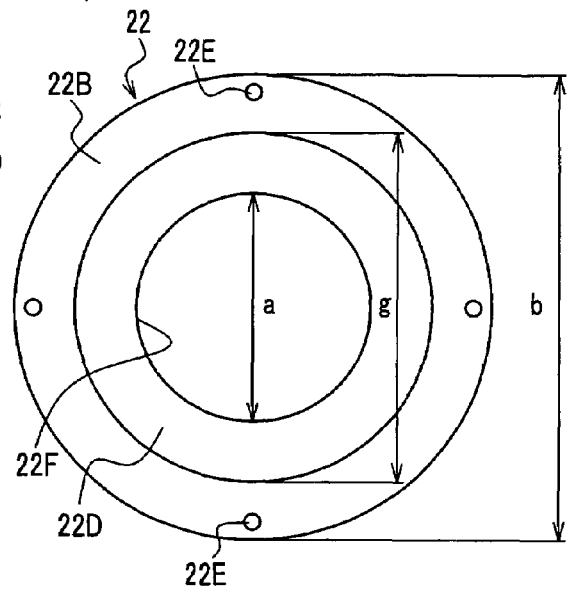
FIG. 9B is a right side view of the second cylindrical phantom.

As shown in FIG. 2 and FIG. 9, the second cylindrical phantom 22 has edge portions 22A and 22B perpendicular to the shaft direction (the term "shaft direction" is described as longitudinal direction in radiology, and the term "perpendicular to the longitudinal direction" is described in transverse direction) at both sides of the shaft direction. One edge portion 22A of the second cylindrical phantom 22 perpendicular to the shaft direction has a stepped portion 22C, which is a fitting portion, formed thereon. In contrast, another edge portion 22B of the second cylindrical phantom 22 perpendicular to the shaft direction has a cylindrical projection 22D, which is another fitting portion, formed thereon. Four through-holes 22E are formed on the cylindrical phantom 22 at equal intervals in the circumference direction. As shown in FIG. 9, the inner diameter of the hollow portion 22F is set to be size a. Consequently, into the hollow portion 22F of the cylindrical phantom 22 can be inserted the column-shaped phantom 12, which has an outer diameter of size a with no space. The depth of the stepped portion 22C of the cylindrical phantom 22 is set to be size f, and the height of the projection of the convex portion 22D for fitting is also set to be size f. The hole size of the stepped portion 22C and the outer diameter size of the convex portion 22D for fitting are set to be size g, respectively.

Figure 10A:
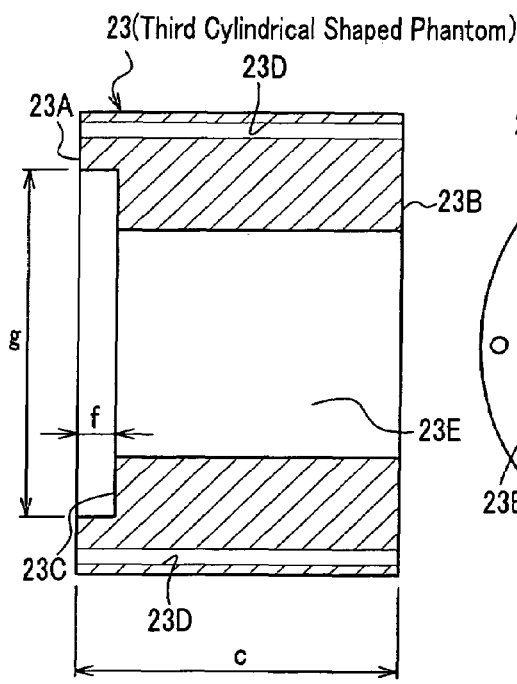
FIG. 10A is a longitudinal cross-sectional view of the third cylindrical phantom.
Figure 10B:
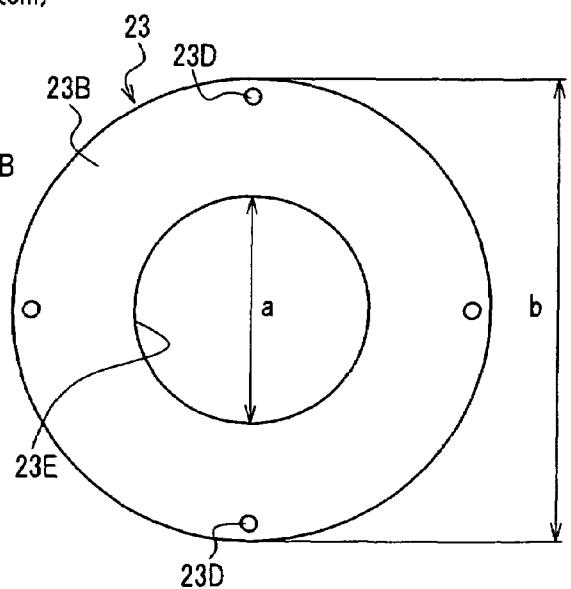
FIG. 10B is a right side view of the third cylindrical phantom.

As shown in FIG. 2 and FIG. 10, the third cylindrical phantom 23 has edge portions 23A and 23B perpendicular to the shaft direction at both sides of the shaft direction. One edge portion 23A of the third cylindrical phantom 23 perpendicular to the shaft direction has a stepped portion 23C, which is a fitting portion, formed thereon. In contrast, another edge portion 23B of the third cylindrical phantom 23 perpendicular to the shaft direction is formed as a ring-shaped flat surface. Four through-holes 23D are formed on the cylindrical phantom 23 at equal intervals in the circumference direction. As shown in FIG. 10, the inner diameter of the hollow portion 23E of the phantom 23 is set to be size a. Consequently, into the hollow portion 23E of the cylindrical phantom 23 can be inserted the column-shaped phantom 13, which has an outer diameter of size a with no space. The outer diameter of the cylindrical phantom 23 is set to be size b, and the length in the shaft direction is set to be size c. The depth of the stepped portion 23C of the cylindrical phantom 23 is set to be size f, and the inner diameter is set to be size g.

Referring to FIG. 1 and FIG. 3, a method for measuring a dose of x-ray irradiated, for example, onto a human head utilizing the phantom assembly 1 of the present invention will be described. As shown in FIG. 3, first, one column-shaped phantom 11, three column-shaped phantoms 12, 12, and 12, and one column-shaped phantom 13 are ready on a bed 3 (see FIG. 1). Then, the convex portion 12C for fitting of the column-shaped phantom 12 is inserted into and fitted to the concave portion 11C. for fitting of the column-shaped phantom 11, and the edge portions 11B and 12A are collided with each other. Here, since the concave portion 11C for fitting of the column shaped phantom 11 is set so as to have a depth of size d, and since the projection size of the convex portion 12C for fitting of the cylindrical phantom 12 is set to be d, these phantoms 11 and 12 are connected without any space. Similarly, with regard to two phantoms 12 and 12, the convex portion 12C for fitting is inserted into and fitted to the concave portion 12D for fitting, whereby they can be connected without any space. Also, with regard to the phantoms 12 and 13, the convex portion 13C for fitting is inserted into and fitted to the concave portion 12D for fitting, whereby they can be connected without any space. In this case, the through-holes 11D, 11E, 12E, 12F, 13D, 13E, 21D, 22E, and 23D provided on the phantoms 11, 12, 13, 21, 22, and 23 connect the connected phantoms 11, 12, 13, 21, 22 and 23 in a straight, respectively.

Next, the device 33 for measuring dose is inserted, for example, in the through-hole 13E provided on the column-shaped phantom 13. The sticks 31 and 32 are inserted into the through-holes 11D, 11E, 12E, 12F, and 13D except for the through-hole 13E having the device 33 for measuring dose inserted therein, to embed the through-holes 11D, 11E, 12E, 12F, 13D and part of the through-hole 13E without any space. In this state, the x-ray radiation from the x-ray CT device 2 is irradiated on the column-shaped phantoms 11, 12, 12, 12, and 13, the dose of the x-ray radiation irradiated onto the human head is measured (deduced).

Subsequently, referring to FIG. 1 and FIG. 4, a method for measuring a dose of x-ray radiation irradiated onto a human body utilizing the phantom assembly 1 of the present invention will be described. First, one cylindrical phantom 21, three cylindrical phantoms 22, 22, and 22, and one cylindrical phantom 23 are ready on a bed 3 (see FIG. 1). Then, the cylindrical projection 21C of the cylindrical phantom 21 is inserted into and fitted to the stepped portion 22C of the cylindrical phantom 22, and the edge portions 21B and 22A are collided with each other. Here, since the projection size of the cylindrical projection 21C of the cylindrical phantom 21 is set to be size f and since the depth of the step of the stepped portion 22C of the cylindrical phantom 22 is also set to be size f, these phantoms 21 and 22 are connected without any space. Similarly, with regard to two phantoms 22 and 22, the cylindrical projection 22D is inserted into and fitted to the stepped portion 22C, whereby they can be connected without any space. Also, with regard to the phantoms 22 and 23, the cylindrical projection 22D is inserted into and fitted to the stepped portion 23C, whereby they can be connected without any space.

Subsequently, the column-shaped phantoms 11, 12, 12, 12, and 13 are inserted step by step from the side of the hollow portion 23E of the cylindrical phantom 23, whereby the column-shaped phantoms 11, 12, 12, 12, and 13 are inserted into the hollow portions of 21E, 22F, 22F, 22F, and 23E without any space, respectively. Subsequently, as shown in FIG. 4, the device 33 for measuring dose is inserted, for example, into the through-hole 13E provided so that it is pierced through the central portion of the column-shaped phantom 13 in the shaft direction. Since total nine through-holes 11D, 11E, 12E, 12F, 13D, 13E, 21D, 22E, and 23D are provided on the phantom assembly 1, the sticks 31 and 32 are inserted into eight through-holes 11D, 11E, 12E, 12F, 13D, 21D, 22E, and 23D except for the through-hole 13E having the device 33 for measuring dose inserted therein, to embed these through-holes without any space. Preferably, the space of the through-hole 13E having the device 33 for measuring dose inserted therein is embedded in the through-holes 11E, and 12F. It should be noted that in the case where the device 33 for measuring dose is inserted at the central portion of the through-hole 13E, the portion of the through-hole which takes up the cable may cause a cable interruption. For this reason, such a stick as that having a shape of the stick 31 or such cannot be inserted. However, since the influence of the space generated at this portion upon the measurement of dose is neglible in the measure, the stick is not necessarily inserted therein.

Here, the stick 31 is configured so that it is inserted, for example, in the through-holes 11D and 12E of the column-shape phantoms 11 and 12 and also inserted in the through-holes 11E and 12F. Similarly, the stick is inserted in the through-holes as for the column-shaped phantoms 12 and 12, for the cylindrical phantoms 22 and 22 and for the cylindrical phantoms 22 and 23.

In this state, the x-ray radiation from the x-ray CT device 2 is irradiated on the column-shaped phantoms 11, 12, 12, 12, and 13, the dose of the x-ray radiation irradiated onto the human body is measured (deduced).

Consequently, according to this embodiment, by suitably connecting the short column-shaped phantoms 11, 12, 12, and 13 and the short cylindrical phantoms 21, 22, 22, 22, and 23 or separating the connected phantom(s) to meet the shape of the beam, the whole length of the phantom assembly 1 can be changed in a step-by-step manner. For this reason, the phantom assembly 1 according to this embodiment can be applicable over all of the dose assessment of the beams from those which have short beam width irradiated from the x-ray CT device from core beams, which have a long beam length.

By setting the whole length of the phantom assembly 1 as a long beam length, at the time of irradiation of x-ray radiation, the scattered radiation generated within the phantom assembly 1 can be captured by the phantom assembly 1 and, thus, the assessment considering the scattered radiation can be made. Consequently, the x-ray dose assessment can be performed in an accurate manner.

Since the column-shaped phantoms 11, 12, 12, and 13 and the cylindrical phantoms 21, 22, 22, 22, and 23 can be separated into pieces from the phantom assembly 1, the space for storing the column-shaped phantoms 11 to 13 and the cylindrical phantoms 21 to 23 can easily be ensured and the transferring can easily be made.

What is more, since the phantom assembly 1 according to the present invention has a configuration that the column-shaped phantoms 11, 12, 12, 12, and 13 and the cylindrical phantoms 21, 22, 22, 22, and 23 are inserted into and fitted with each other by inserting the convex portions 12C and 13C for fitting into the concave portions 11C and 12D to be fitted with each other, and/or when the projection size d, for example, of the convex portion 12C of the phantom 12 to be fitted is made to a minus allowance relative to the depth d, for example, of the concave portion 11C for fitting of the phantom 11 so that edge portions 11B and 12A can be closely contact with each other, an amount of x-ray radiation passing through a space, for example, between the edge portion 11B of the column-shaped phantom 11 and the edge portion 12A of the column-shaped phantom 12, and a space, for example, between the edge portion 12B of the column-shaped phantom 12 and the edge portion 13A of the column-shaped phantom 13 can be markedly decreased. This also makes it possible to perform x-ray dose assessment in a much more accurate manner.

Similarly, when the cylindrical phantoms 21, 22, 22, 22, and 23 are fitted to each other, it becomes difficult to pass the x-ray radiation form a space, for example, between the edge portion 21B of the cylindrical phantom 21 and the edge portion 22A of the cylindrical phantom 22, and a space, for example, between the edge portion 22B of the cylindrical phantom 22 and the edge portion 23A of the cylindrical phantom 23. This also makes it possible to perform x-ray dose assessment in a much more accurate manner.

Also, as described above, since it is configured that the column-shaped phantoms 11, 12, 12, 12, and 13 are tightly connected (fitted) to each other by inserting the convex portions 12C and 13C for fitting into the concave portions 11C and 12D for fitting, these phantoms 11, 12, 12, 12, and 13 can be fixed in a stable manner. By inserting acrylic sticks through these holes, the phantoms were more tightly fixed to each other.

Furthermore, since it is configured that the stick 31 is inserted into a plurality of through-holes of the column-shaped phantoms, i.e., through-holes 11D and 11E of the column-shaped phantom 11, and through-holes 12E and 12F of the column-shaped phantom 12, the column-shaped phantoms can be connected by the stick 31 in much more tight manner. Similarly, when the stick 31 is inserted into a plurality of through-holes of the cylindrical phantoms, the cylindrical phantoms 21 and 22, the cylindrical phantoms 22 and 22, and the cylindrical phantoms 22 and 23 can also be much more tightly fixed.

Figure 12:
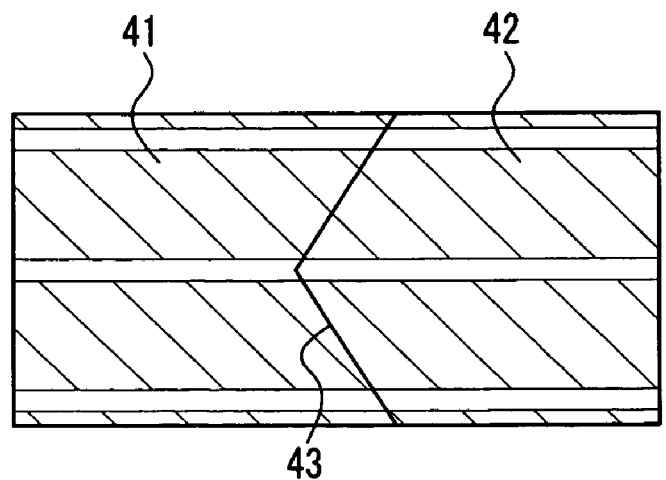
FIG. 12 is a longitudinal view showing column-shaped phantoms according a first variant of the present invention in the state where they are assembled.
Figure 13:
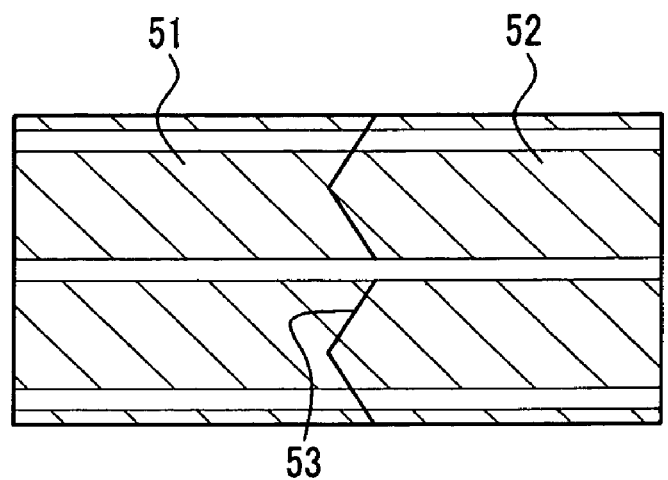
FIG. 13 is a longitudinal view showing column-shaped phantoms according a second variant of the present invention in the state where they are assembled.

In the foregoing embodiments, while the collision surface between the column-shaped phantoms 11 and 12 is configured to be formed into a stepped shaped, it should be noted that the present invention is not restricted thereto. For example, as shown in FIG. 12, which shows a first variant, a collision surface 43 between column-shaped phantoms 41 and 42 may be formed into a tapered shape where the collision surface 43 is slanted. Also, as shown in FIG. 13, which shows a second variant, a collision surface 53 between column-shaped phantoms 51 and 52 may be formed into a cone shape.

Also, in the foregoing embodiments, the case where three column-shaped phantoms 12 are utilized has been exemplified, the present invention is not restricted thereto. For example, four or more phantoms or two phantoms may be used to meet the shape of the x-ray. Also, the column-shaped phantoms 12 may not used and the column-shaped phantoms 11 and 13 may be directly connected.

Furthermore, in the foregoing embodiments, the case where three cylindrical phantoms 22 are utilized has been exemplified, the present invention is not restricted thereto. For example, four or more phantoms or two phantoms may be used to meet the shape of the x-ray. Also, the cylindrical phantoms 22 may not used and the cylindrical phantoms 21 and 23 may be directly connected.

Also, in the foregoing embodiments, the case where the device 33 for measuring dose is inserted into the through-hole 13E has been exemplified, the present invention is not restricted thereto. For example, one or more device(s) 33 for measuring dose may be inserted into one or more of through-hole(s) 11D, 11E, 12E, 12F, 13D, 21D, 22E, and 23D.

While the phantom assembly where the column-shaped phantoms 11 to 13 are inserted into the cylindrical phantoms 21 to 23 has been exemplified to be used for assessment for a head portion, the present invention is not restricted thereto. For example, column-shaped phantoms having an outer diameter substantially the same as that of the cylindrical phantoms are produced and they may be connected for use in assessment of body.

Also, the hole size (inner diameter) of each of the through-holes 11D, 11E, 12E, 12F, 13D, 13E, 21D, 22E, and 23D may be determined so to meet the outer shape of the device 33 for measuring dose, and the hole size (inner sizes) of each of the hollow portions 21E, 22F, and 23E may be determined so as to the outer sizes a of each of the column-shaped phantoms 11, 12 and 13. The number of through-holes 11D, 11E, 12E, 12F, 13D, 13E, 21D, 22E, and 23D may be determined depending upon the object of the measurement.

What is claimed is:

1. An apparatus for outputting a dose measurement result, comprising:
    a phantom extending in a direction, the phantom comprising
        edge portions at both ends, in the direction, of the phantom;
        a material for attenuating a radiation into the phantom;
        a fitting portion formed on at least one of the edge portions;
        a plurality of through-holes in the material extending in the direction between the edge portions inclusively, said plurality of through-holes extending to the fitting portion; and
    a dose detector in at least one of the through-holes and configured to measure a dose of the radiation through the material and to output the dose measurement result.

2. The apparatus according to claim 1, wherein the phantom comprises a cylindrical shape, and wherein one of the plurality of through-holes is located at a central portion thereof for housing the dose detector.

3. The apparatus according to claim 1, wherein the phantom comprises a sleeve-shape extending in the direction having a hollow portion therein extending in the direction for housing an external phantom.

4. The phantom according to claim 1, wherein the fitting portion fits in a corresponding fitting portion of an external phantom.

5. The phantom according to claim 1, wherein the plurality of through-holes extends continuously between the edge portions inclusively.

6. The phantom according to claim 1, wherein
    the phantom comprises a ring portion as the fitting portion and a body having a cylindrical circumferential surface, and wherein
    the ring portion has a circumferential surface and a fitting space either therein in which the circumferential surface is continuously connected to the cylindrical circumferential surface or between the cylindrical circumferential surface and the circumferential surface.

7. A phantom assembly for outputting a dose measurement result, comprising:
    a plurality of phantoms, each phantom extending in a direction and comprising edge portions at both ends, in the direction, of the phantom, a material for attenuating a radiation into the phantom, a fitting portion formed on at least one of the edge portions, and a plurality of through-holes in the material extending in the direction between the edge portions inclusively, said plurality of through-holes extending to the fitting portion; and
    a dose detector in at least one of the through-holes and configured to measure a dose of the radiation through the material and to output the dose measurement result, wherein the phantoms are connected with each other to have contact therebetween at the fitting portions thereof.

8. A phantom assembly according to claim 7, further comprising:
    at least one stick inserted into at least one of the through-holes for embedding the at least one of the through-holes.

9. The phantom assembly according to claim 8, wherein the at least one stick is arranged across two or more phantoms.

10. The phantom assembly according to claim 7, wherein each phantom has a cylindrical shape, and wherein one of the through-holes is located at a central portion thereof for housing the dose detector.

11. A phantom assembly for outputting a dose measurement result, comprising:
    a plurality of first phantoms, each first phantom extending in a first direction and comprising edge portions at both ends, in the first direction, of the first phantom, a material for attenuating a radiation into the first phantom, a column shape, a first fitting portion on at least one of the edge portions of the first phantom, and a plurality of through-holes in the material extending in the first direction between the edge portions of each first phantom inclusively, wherein the first phantoms are connected with each other at the first fitting portions; and
    a plurality of second phantoms, each second phantom extending in a second direction and comprising edge portions at both ends, in the second direction, of the second phantom, the material for attenuating the radiation into the second phantom, a sleeve shape comprising a hollow portion therein at both ends, in the second direction, of the second phantom, a second fitting portion formed on at least one of the edge portions of the second phantom, and a plurality of through-holes in the material extending in the second direction between the edge portions of each second phantom inclusively, wherein the second phantoms are connected with each other at the second fitting portions and house the first phantoms; and
    a dose detector in at least one of the through-holes and configured to measure a dose of the radiation through the material and to output the dose measurement result.

12. The phantom assembly according to claim 11, wherein the one of the through-holes of each of the first phantoms is located at a central portion thereof for housing the dose detector in the hollow portions.

13. The phantom assembly according to claim 11, further comprising at least one stick for embedding at least one of the through-holes of the first and second phantoms.

14. The phantom assembly according to claim 13, wherein the stick is arranged across two or more of the first phantoms.

15. The phantom assembly according to claim 13, wherein the stick is arranged across two or more of the second phantoms.

* * * * *